United States Patent
Fengler et al.

(10) Patent No.: US 7,420,151 B2
(45) Date of Patent: Sep. 2, 2008

(54) DEVICE FOR SHORT WAVELENGTH VISIBLE REFLECTANCE ENDOSCOPY USING BROADBAND ILLUMINATION

(75) Inventors: John J. P. Fengler, North Vancouver (CA); Paul R. Westwick, Vancouver (CA); Joachim W. Boehm, North Vancouver (CA)

(73) Assignee: Novadaq Technologies Inc., Mississauga, Ontario (CA)

( * ) Notice: Subject to any disclaimer, the term of this patent is extended or adjusted under 35 U.S.C. 154(b) by 157 days.

(21) Appl. No.: 11/546,013

(22) Filed: Oct. 10, 2006

(65) Prior Publication Data

US 2007/0102623 A1    May 10, 2007

Related U.S. Application Data

(60) Provisional application No. 60/727,479, filed on Oct. 17, 2005.

(51) Int. Cl.
*A61B 1/04* (2006.01)

(52) U.S. Cl. .......... 250/208.1; 250/226; 600/160; 348/71; 348/222.1

(58) Field of Classification Search .......... 250/208.1, 250/226; 600/109, 112, 160; 348/71, 222.1, 348/272, 575
See application file for complete search history.

(56) References Cited

U.S. PATENT DOCUMENTS

| 4,742,388 A | 5/1988 | Cooper |
| 4,799,104 A * | 1/1989 | Hosoya et al. ............. 348/71 |
| 6,529,239 B1 | 3/2003 | Dyck |
| 6,750,971 B2 | 6/2004 | Overbeck |
| 2002/0196335 A1 | 12/2002 | Ozawa |
| 2006/0241496 A1* | 10/2006 | Fengler et al. ........... 600/476 |

* cited by examiner

*Primary Examiner*—Kevin Pyo
(74) *Attorney, Agent, or Firm*—Rissman Jobse Hendricks & Oliverio

(57) ABSTRACT

A system for performing short wavelength imaging with a broadband illumination source includes an image processor that receives signals from a color image sensor. The image processor reduces the contribution of red illumination light to an image by computing blue, green, and blue-green (cyan) color components of display pixels from the signals received from the image sensor. The blue, green, and cyan color component values are coupled to inputs of a color monitor for display to produce a false color image of the tissue.

17 Claims, 8 Drawing Sheets

DEVICE FOR SHORT WAVELENGTH VISIBLE REFLECTANCE ENDOSCOPY USING BROADBAND ILLUMINATION

CROSS-REFERENCE TO RELATED APPLICATION

The present application claims the benefit of U.S. Provisional Application No. 60/727,479, filed Oct. 17, 2005, which is herein incorporated by reference.

FIELD OF THE INVENTION

The present invention relates to medical imaging systems, and in particular, to systems for viewing internal body tissues of patients.

BACKGROUND

In an effort to detect and treat diseases, many physicians are using minimally invasive imaging techniques to view the internal body tissues of patients. Such techniques typically employ imaging devices such as video endoscopes, which are inserted into the patient and used to obtain images of the tissue. Such images are most commonly color images of reflected white light, where the image is composed of light from the entire visible spectrum. These images are typically displayed on a color video monitor.

A new imaging technique that may prove useful in detecting disease is one in which images are generated from a subset of wavelengths in the visible spectrum and, in particular, from blue and green wavelengths in the visible spectrum. In this imaging technique, tissue is illuminated with blue-green light which is preferentially absorbed by blood. As a consequence, superficial blood vessels appear dark in the resulting reflected light image. In addition, the blue-green light does not penetrate tissue and scatter as much as red light and, thereby, provides more detailed structural information about the tissue surface. Since the onset of diseases, such as cancer, are frequently accompanied by changes in tissue surface morphology and an increase in vascularity to support rapidly proliferating cells, such an imaging technique may be particularly useful in identifying early cancerous or precancerous lesions.

A conventional means of achieving such an imaging technique involves the use of specialized endoscopic light sources that are equipped with one or more filters to restrict the spectrum of illumination light to light in the blue-green wavelength band. However, because physicians often want to utilize both the full spectrum white light and the restricted spectrum, short wavelength imaging modes, such filters are generally incorporated into a mechanism which moves them into and out of the light path and thereby increases the cost and complexity of the light source. It is therefore desirable for an endoscopic imaging system not to require the incorporation and movement of filters to produce the light for the two different imaging modes, but still allow physicians to utilize the same light source for a full spectrum white light imaging mode and a restricted spectrum, short wavelength imaging mode.

SUMMARY

The present invention is a system for imaging tissue with a light source that allows physicians to utilize the same light source for a full spectrum white light imaging mode and a restricted spectrum, short wavelength imaging mode, but does not to require the incorporation and movement of filters in the light source to produce the light for the two different imaging modes. The present invention utilizes the color imaging capabilities of a video image sensor and image processing techniques to restrict the displayed color video image information to image information from the blue and green reflected light received by the video image sensor.

In one embodiment of the invention, the video endoscope image signals are produced by an RGB color image sensor having pixels that are sensitive to red, green, and blue light. Signals from the pixels that are sensitive to green and blue light are used to create a false color image of the tissue. This false color image is generated by a video processor which couples the signals obtained from the pixels that are sensitive to blue and green light, respectively, to two of the color inputs of a color video monitor, and couples a combination of the signals produced from the pixels that are sensitive to blue and green light to a third color input of the color video monitor.

In another embodiment of the invention, the video endoscope image signals are produced by a CMYG color image sensor. In this embodiment, signals from the pixels that are sensitive to complementary colors (cyan, magenta, yellow) and green are combined by the video processor in such a way so as to substantially eliminate the contribution of reflected red light to the displayed color video image. In one embodiment of the invention, a transformation matrix converts luminance and red and blue chroma difference signals into blue, cyan, and green color signals that are supplied to color inputs of a color monitor.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

As indicated above, the present invention is an endoscopic system for imaging tissue that utilizes broadband illumination for both full spectrum, white light imaging and restricted spectrum, short wavelength imaging. In the latter imaging mode, the invention described herein utilizes video processing to remove or reduce the contribution of reflected red illumination light to the displayed color video image. Since full spectrum, white light imaging technologies are well established, the description of the invention will be limited to techniques to enable restricted spectrum, short wavelength imaging using image processing.

Figure 1:
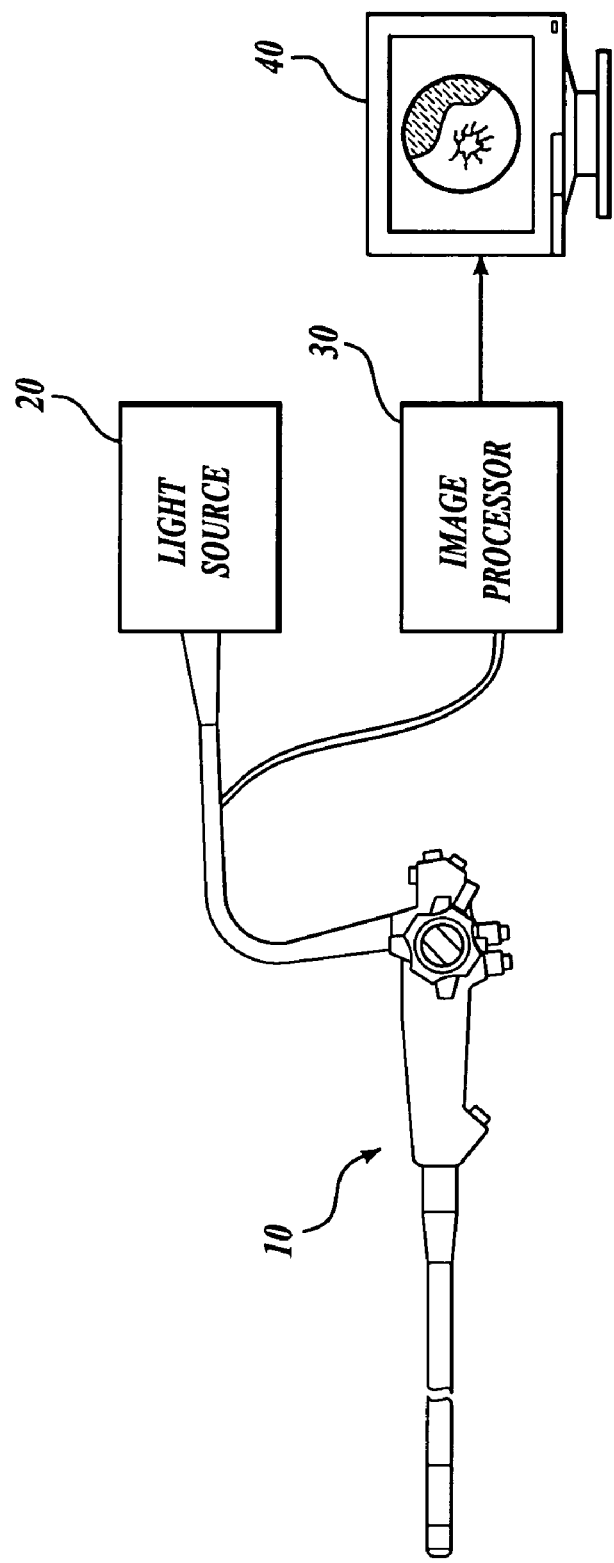
FIG. 1 illustrates a video endoscopic imaging system in accordance with one embodiment of the present invention.

FIG. 1 shows one embodiment of an endoscopic imaging system suitable for use with a present invention. The system contains a video endoscope 10 which receives illumination light from a light source 20. Light from the light source 20 is directed by the endoscope into the patient's body where it reflects off a tissue sample. Light is collected by an objective lens system in the endoscope 10 and directed onto an image sensor. Signals from the image sensor are received by a video processor 30 that produces video images of tissue for display on a video monitor 40 or recording on a video tape, DVD, etc. In one embodiment of the invention, the image sensor is located at the distal tip of the endoscope 10. In alternative embodiments in the invention, the endoscope may include one or more imaging fibers that carry an image to an external image sensor.

In one embodiment of the invention, the light source 20 produces a broadband illumination light that is used for both color (i.e., white light) imaging and short wavelength imaging, as will be described in further detail below. The short wavelength imaging mode is useful for producing images of tissue from the blue-green portion of the reflected light spectrum.

Figure 2A:
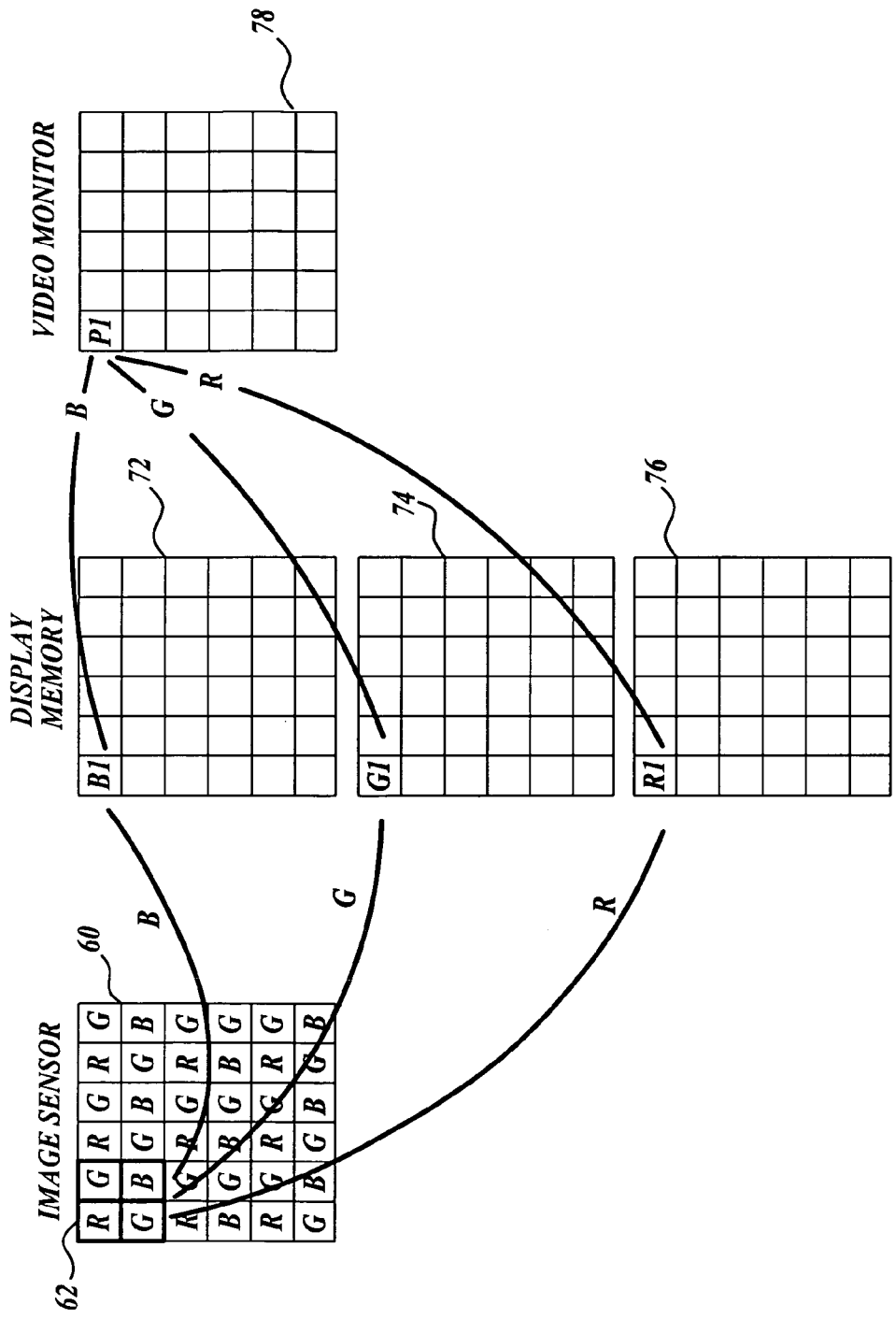
FIGS. 2A-2B illustrate a conventional Bayer pattern RGB image sensor and technique for computing display pixels.
Figure 2B:
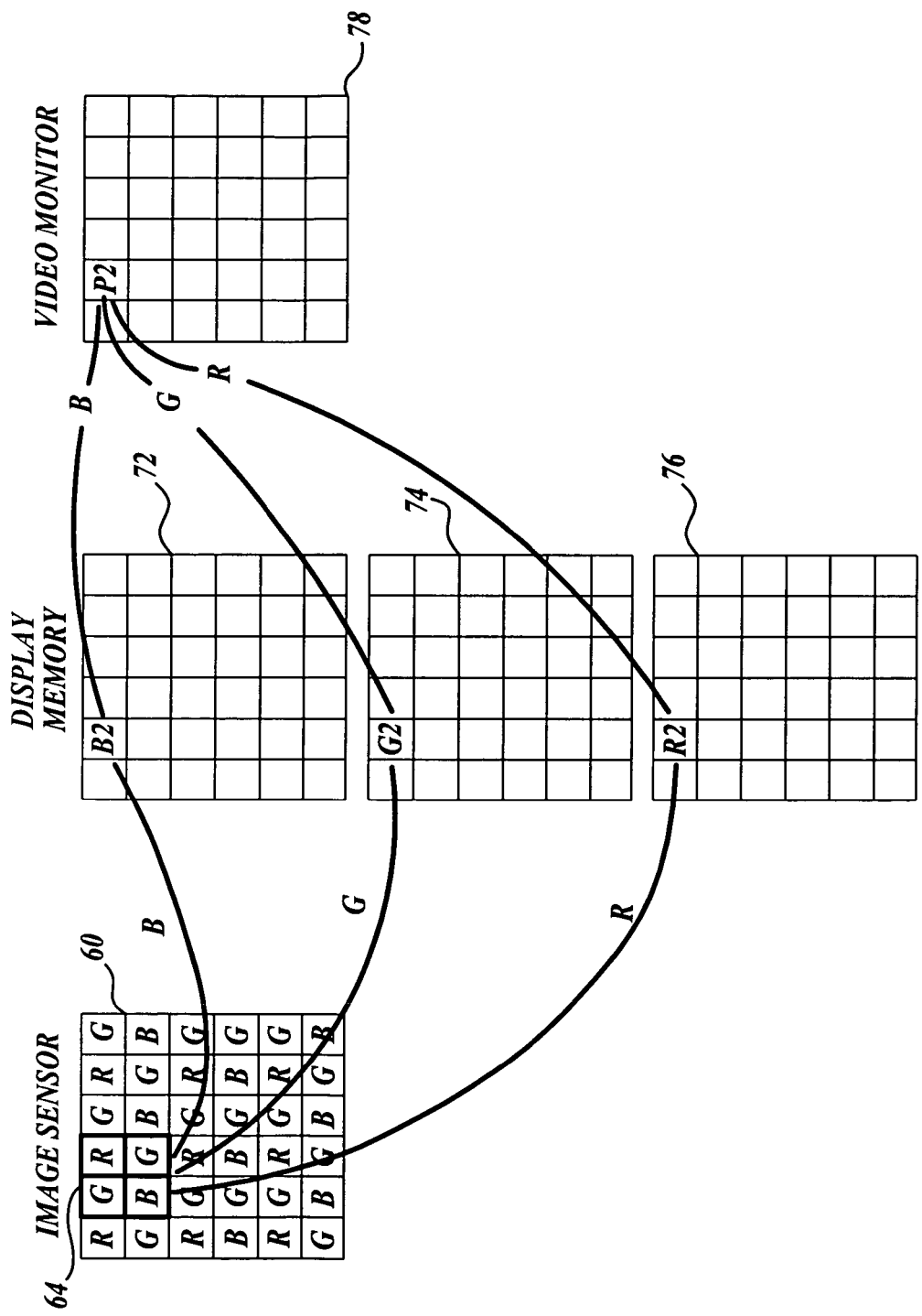

FIG. 2A illustrates one embodiment of a color image sensor that may be used in a video endoscope system for performing the short wavelength imaging with a broadband illumination source in accordance with the present invention. In the embodiment shown, the color image sensor 60 is an RGB type image sensor having a number of pixels that are covered with a mosaic filter that passes light in the red, green, or blue spectral bands. The light passing into the sensor generates an electron charge in the pixel under each filter in proportion to the amount of light in that part of the spectrum. Red, green, and blue image signals are subsequently generated by the video processor based upon the charge stored in each to the image sensor pixels. The manner in which the charge in the pixels is converted into red, green, and blue image signals is dependent on the specific pattern of the RGB filter mosaic and the (charge) read-out architecture of the image sensor. For full spectrum white light imaging with an image sensor having a Bayer pattern, as shown in FIG. 2A, groups of pixels from the image sensor are typically used to determine the color of a corresponding display pixel contained in an image of the tissue. In the example shown, a group of pixels 62 is analyzed to compute the color of a display pixel P1, and an overlapping group of pixels 64, as shown in FIG. 2B, is analyzed to compute the color of a display pixel P2. After any additional desired image processing, the color image signal values generated for each display pixel are typically placed into a blue color display memory 72, a green color display memory 74, and a red color display memory 76 in the video processor. These color display memories are coupled to the corresponding blue, green, and red signal inputs of a color video monitor 78 that is used to display the color video image.

Figure 2C:
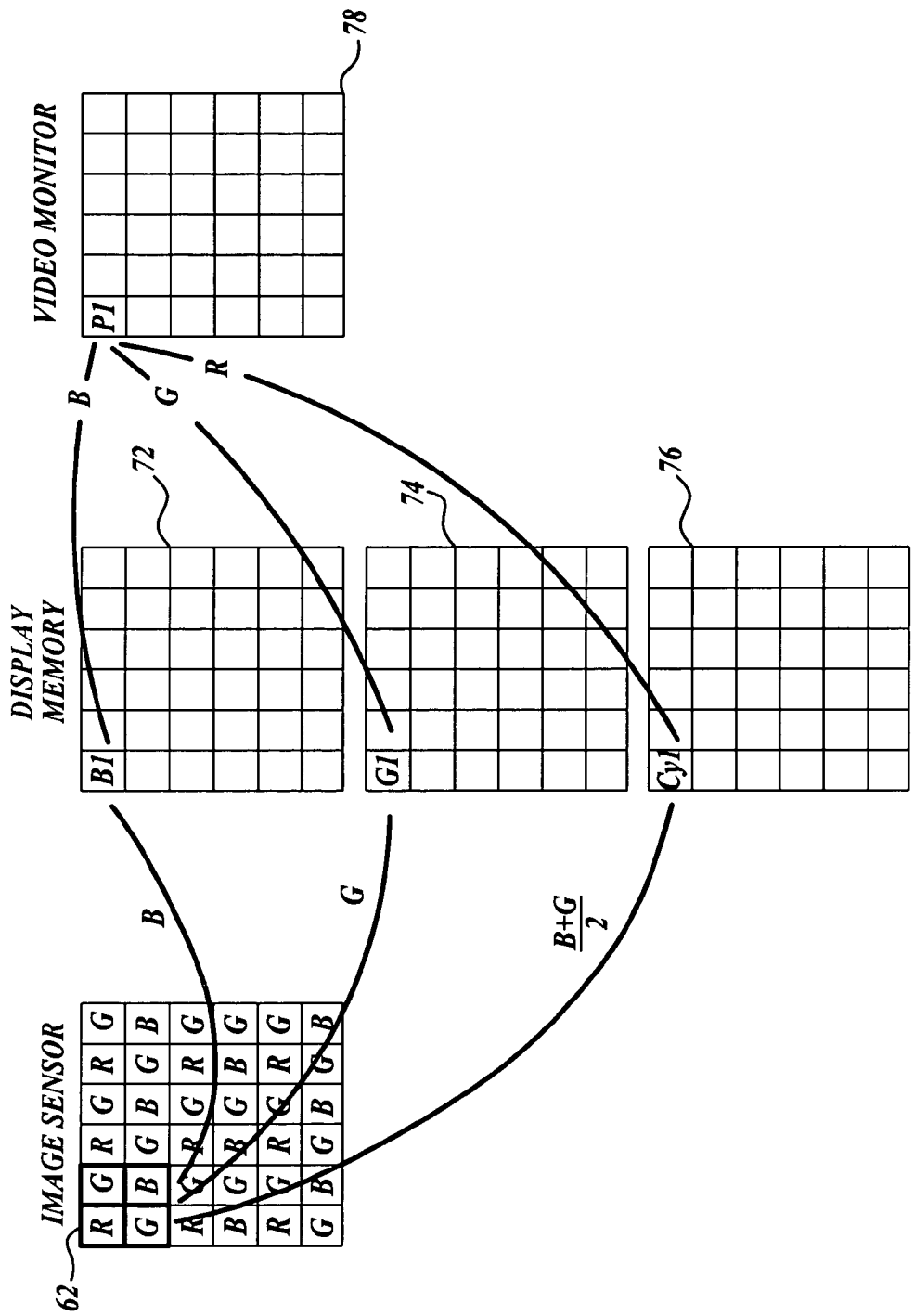
FIG. 2C illustrates a technique for performing restricted spectrum, short wavelength imaging in accordance with one embodiment of the invention.
Figure 3:
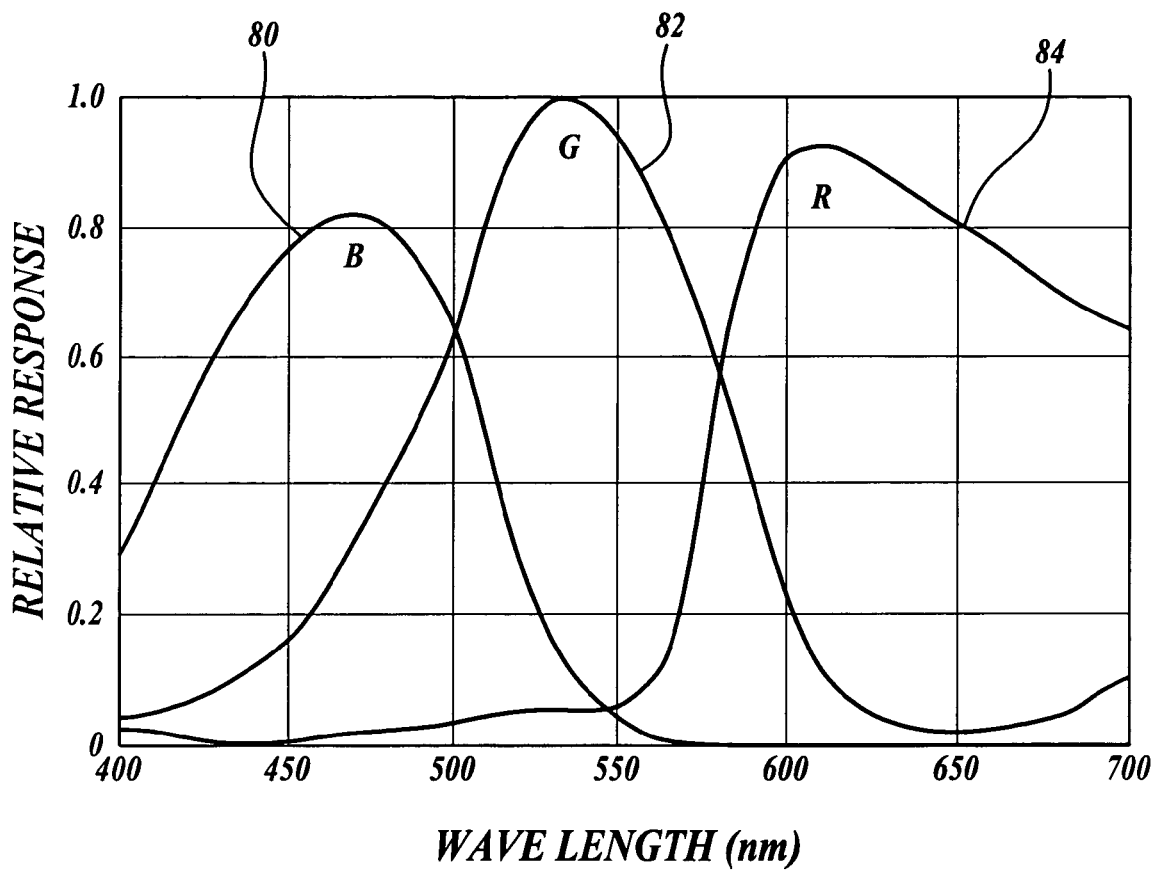
FIG. 3 illustrates the typical spectral responses of the mosaic filters in an RGB image sensor.

FIG. 3 illustrates a typical spectral response 80 of the mosaic filter that passes blue light, a typical spectral response 82 of a mosaic filter that passes green light, and a typical spectral response 84 of a mosaic filter that passes red light to the pixels in the RGB color image sensor 60. Because the passbands of the red mosaic filters do not significantly overlap with the passbands of the other filters for a short wavelength imaging mode, the contribution of the image signals due to red illumination light can be reduced or largely eliminated by not assigning the image signals produced by image sensor pixels that are sensitive to red light to their corresponding display pixels. In one embodiment of the invention illustrated in FIG. 2C, the assignment of color image signal values to the red, green, and blue color display memories is altered from that for white light imaging to achieve a short wavelength imaging mode. Specifically, for a short wavelength imaging mode, the blue and green image signals may be generated directly from the blue and green sensitive pixels of the RGB image sensor, and a 'cyan' signal value may be computed from a combination of the signals produced by the pixels sensitive to blue and green light. In one embodiment, the average of the signals produced by the pixels sensitive to blue and green light is used as a cyan color component of the display pixels. In this embodiment, therefore, the blue, green, and cyan image signals are stored in the color display memories 72, 74, 76 of the video processor, respectively, for connection to the color inputs of the color video monitor 78.

Which of the blue, green, and cyan image signals are stored in which color display memory or how the color display memories 72, 74, 76 are coupled to the inputs of a color video monitor 78 is a matter of individual preference and may be configured in different ways. In one embodiment, the image signals are assigned to the color display memories as described above, and the color display memory 74 is coupled to the red input of the color video monitor, the color display memory 72 is coupled to the blue input of the color video monitor, and the memory 76 that stores the cyan image signals is coupled to the green input of the color video monitor. However, blue, green, and cyan image signals may be assigned to the color display memories differently, or the color memories 72, 74, and 76 could, if desired, be coupled to the inputs of the color video monitor differently.

Figure 4:
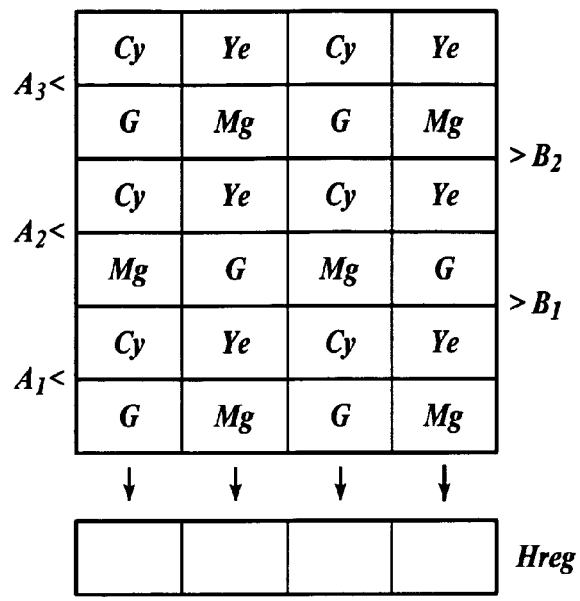
FIG. 4 illustrates the read-out of a CMYG color image sensor.
Figure 5:
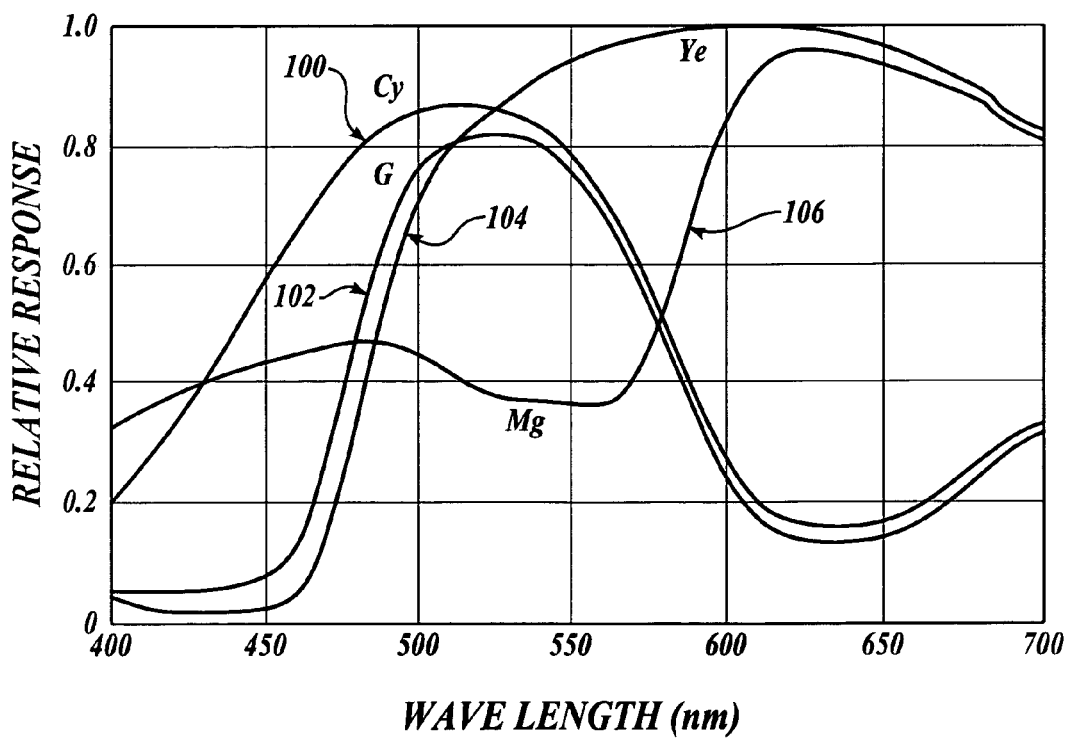
FIG. 5 illustrates the typical spectral responses of the mosaic filters in a CMYG image sensor.

In another embodiment of the invention, the short wavelength imaging mode is accomplished using broadband illumination and a color image sensor with a complimentary color filter mosaic such as a CMYG (cyan, magenta, yellow, and green). Such filter mosaics are commonly used in consumer and medical electronics where imaging is formed with a single color image sensor. FIG. 4 illustrates a pattern of cyan (Cy), yellow (Ye), magenta (Mg), and green (G) pixels in a CMYG color image sensor. FIG. 5 illustrates a typical spectral curve 100 indicating the response of the cyan pixels to light. A typical curve 102 indicates the response of the green pixels to light. A typical spectral curve 104 indicates the response of the yellow pixels to light, while a typical spectral curve 106 indicates the response of the magenta pixels to light. In a CMYG-type color image sensor, the color components of a display pixel are generally computed from luminance (Y) and red and blue chroma difference signals (Cr, Cb), and the spectral properties of the cyan, magenta, yellow, and green mosaic filters are typically selected to facilitate the generation of the luminance and chroma difference signals.

As will be appreciated by viewing the response curves of FIG. 5, none of the filters completely remove a red component (i.e., greater than 600 nanometers) of the light received by the CMYG image sensor. In operation, the CMYG image sensor is typically read out two lines at a time, and the resulting summed pixel values are used to compute the luminance and chroma difference ($YC_rC_b$) signals. The computation of such signals is considered to be well known to those of ordinary skill in the art. However, a brief description of how the signals are computed is described herein.

Complimentary color mosaic image sensors (i.e., CMYG sensors) generally have a pattern of optical filters deposited over the CCD pixel array, as shown in FIG. 4. When light hits the image sensor, charge is collected in the pixels beneath the color filter mosaic. During the read-out period, the charge is transferred out of the image sensor and into a transfer register (Hreg) as a series of lines. As a line of charge is read into the transfer register, the remaining lines of charge in the image sensor are shifted one line closer to the transfer register so that a subsequent line (e.g., $A_2$) may be read into the transfer register after the transfer register has been emptied. After a line of charge is read into the transfer register, it is transferred out of this register before the next line is read in.

For a CMYG filter mosaic image sensor, however, each "line" of charge read out is actually a pair of lines within the image sensor. Vertically adjacent pixel pairs, therefore, get summed upon readout. For line $A_1$, the summed pixels in the transfer register are as shown below.

| $A_1$ | Cy + G | Ye + Mg | Cy + G | Ye + Mg | Hreg |

These summed pixel values constitute the values of the first line in field A. Line $A_2$ will sum charge from pixels with different filter colors as shown below:

| $A_2$ | Cy + Mg | Ye + G | Cy + Mg | Ye + G | Hreg |

Line $A_3$ will again sum pixels of the same color as line $A_1$.

After the image sensor has been read out to form a complete image field A, charge is again allowed to collect in the pixels, and field B is read out. The lines in field B are vertically staggered (or "interlaced") sums of pixels compared to those read out for field A as shown in FIG. 4.

An array of virtual pixels is constructed from each field of pixels read out from the image sensor. The signal level for each of these virtual pixels is defined in terms of brightness and color by a luminance (Y) value and two chroma difference values (the red chroma difference value, $C_r$, and the blue chroma difference value, $C_b$). Each virtual pixel is constructed from the charge values for a quadrant of image sensor pixels. The luminance and chroma difference values are then calculated for the next virtual pixel from the next overlapping quadrant of pixels as shown below, and this is repeated for each quadrant in line $A_1$.

As described previously, the charge in the image sensor pixels is vertically summed when the image sensor is read out such that line $A_1$ will consist of the charge sums in the transfer register Hreg, as shown in the figure again below:

| $A_1$ | Cy + G | Ye + Mg | Cy + G | Ye + Mg | Hreg |

Each quadrant in the image sensor is now represented by consecutive pairs of pixels in the transfer register. The charge values in these pairs of transfer register pixels is then used to calculate the luminance and chroma difference values for a virtual pixel as follows:

The luminance value Y for the virtual pixel is defined as half of the sum of the charges in the first consecutive pair of pixels in the transfer register (the sum of the charges in the first image sensor quadrant).

$$Y=\{(Cy+G)+(Ye+Mg)\}\times\tfrac{1}{2}$$

The red chroma difference value $C_r$ is defined as the difference between consecutive pairs of pixels in the transfer register.

$$C_r=\{(Ye\ 30\ Mg)-(Cy+G)\}$$

It should be noted that only one chroma difference value can be calculated directly from a given quadrant of pixels in the image sensors and that red and blue chroma difference signals are calculated on alternate lines for each field. For field A, the red chroma difference value can be computed from the charge sums in quadrants for odd number lines $A_1$, $A_3$, . . . , and blue chroma difference values are calculated from the charge sums in quadrants for even number lines $A_2$, $A_4$, . . . .

The luminance calculation for this first virtual pixel of line $A_2$ is the same (one half of the sum of consecutive pixels in the transfer register), but the chroma difference value calculation now produces a blue chroma difference value.

$$C_b=\{(Cy+Mg)-(Ye+G)\}$$

Given the pattern of the CMYG color filter mosaic, each quadrant of pixels on line $A_2$ will yield a luminance and blue chroma difference value whereas for the odd numbered lines $A_1$, $A_3$, . . . will yield a luminance value and a red chroma difference value. To obtain a red chroma difference value for the first virtual pixel in line $A_2$, the value is interpolated from the red chroma difference values for the first virtual pixel in lines $A_1$ and $A_3$. Likewise, blue chroma difference values are calculated for odd numbered lines by interpolating blue chroma difference values from the vertical adjacent quadrants on even-numbered lines.

Figure 6:
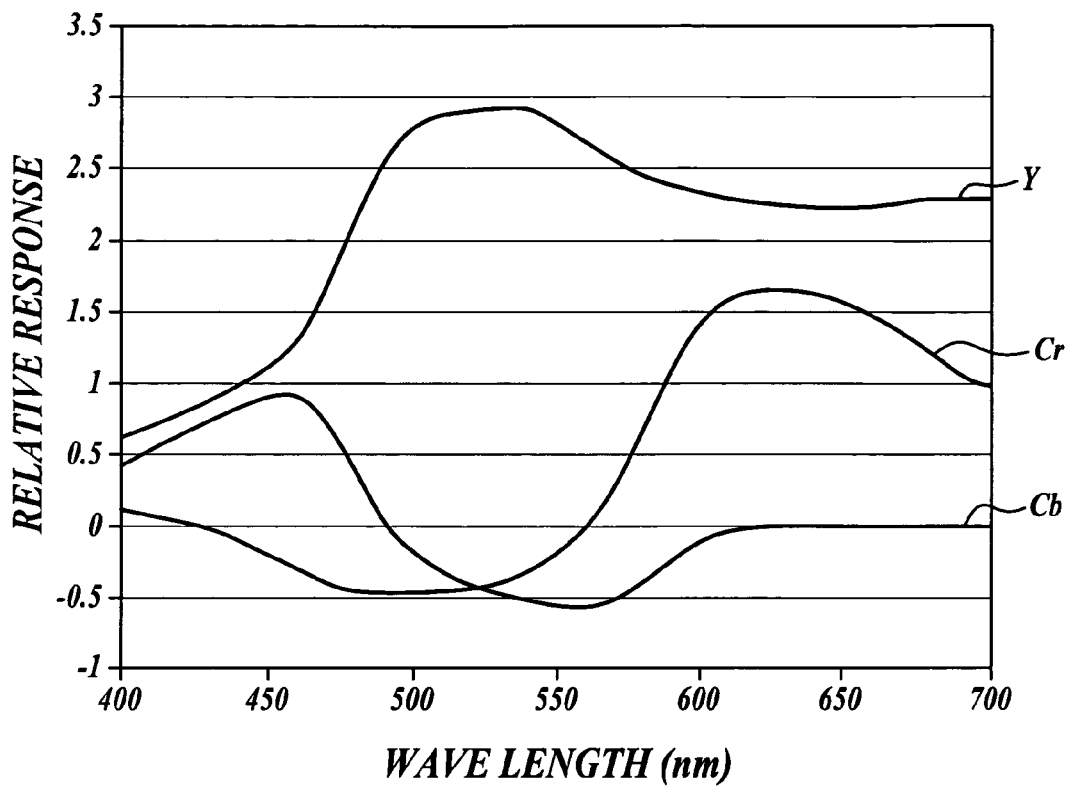
FIG. 6 illustrates a typical spectral response of the luminance and red and blue chroma difference signals from a CMYG image sensor.

FIG. 6 illustrates a typical response of the luminance Y, red chroma difference $C_r$, and blue chroma difference $C_b$ to received wavelengths of light. As can be seen in FIG. 6, the blue chroma difference signal $C_b$ has a value of approximately zero in the red wavelength region. That is, the signal $C_b$ has a value of approximately zero for wavelengths greater than 600 nanometers. The luminance signal Y is generally constant in the red portion of the spectrum, and the red chroma difference signal $C_r$, although not constant, can be roughly approximated as contributing two-thirds as much to the total signal response as the luminance signal Y.

In conventional color image processing, the luminance and chroma difference signals are converted to red, green, and blue image signals that are displayed on a color monitor with a matrix that multiplies each of the luminance and chroma difference signals by the appropriate values to generate corresponding red, green, and blue color component values. Nominal values for such matrix coefficients are typically determined by the sensor manufacturer, but these can typically be modified in order to produce the appropriate white balance or other color correction required to display an image in its true color on a monitor.

In one embodiment of the invention, in which the video endoscope utilizes a CMYG color image sensor, the contribution of red illumination light to the displayed video image is substantially reduced or eliminated by calculating and displaying only the green, cyan, and blue image signals from the luminance and chroma difference signals produced with the image sensor. In this embodiment, the green, cyan, and blue image signal values are calculated by modifying the color space transformation matrix normally used to generate red, green, and blue (RGB) image signal values from luminance and chroma difference (YC$_r$C$_b$) signals. For the luminance and chroma difference response curve similar to that shown in FIG. 6, the color space transformation matrix coefficients are selected such that the contribution of the red chroma difference signals to any of the blue, cyan, or green signals is approximately −1.5 times the contribution of the luminance signal. In this manner, the contribution of the red image information from the red chroma difference signal and the luminance image signal will substantially cancel each other. Furthermore, since cyan is located somewhere between blue and green in the spectrum, the color space transformation matrix coefficients used to generate the Cy (cyan) image signal can be approximated as an arithmetic mean of the coefficients for the blue and green signals. One matrix of coefficients for generating the blue, cyan, and green signals from the luminance and chroma difference signals can be constructed as follows.

$$\begin{vmatrix} G \\ Cy \\ B \end{vmatrix} = \begin{bmatrix} 1 & -1.5 & 1 \\ 1 & -1.5 & 4 \\ 1 & -1.5 & 6 \end{bmatrix} \begin{vmatrix} Y \\ C_r \\ C_b \end{vmatrix}$$

Ideally the blue, cyan, and green image signals should be composed entirely of responses restricted, respectively, to the blue, cyan, and green parts of the visible spectrum. This can be achieved to the extent that the YC$_r$C$_b$ response curves, shown in FIG. 6, can be combined so as not to produce a significant negative response to light from other parts of the visible spectrum. In generating the blue (B) image signal, therefore, it can be seen that by summing the contributions of Y, C$_r$, and C$_b$ curves in the green (~550 nm) part of the spectrum, the coefficient for the C$_b$ value is constrained to be a nominal value of ~6, if the coefficients for the Y and C$_r$ values are 1 and −1.5, respectively. If the coefficient for the C$_b$ value used to generate the blue (B) image signal is significantly larger than 6 (and the coefficients for the Y and C$_r$ values remain 1 and −1.5, respectively), the summed contributions of Y, C$_r$, and C$_b$ responses to the blue (B) image signal in the green (~550 nm) part of the spectrum would have a significant negative value. Such a negative value would result in the undesirable consequence of diminishing of the blue image signal whenever green (i.e., 550 nm) light was present.

If the coefficient for the C$_b$ value used to generate the blue (B) image signal is significantly smaller than 6 (and the coefficients for the Y and C$_r$ values remain 1 and −1.5, respectively), the summed contributions of Y, C$_r$, and C$_b$ responses to the blue (B) image signal in the green (~550 nm) part of the spectrum would have a significant positive value. Such a positive value would result in the undesirable consequence of augmenting the blue image signal whenever green (i.e., 550 nm) light was present.

Similar rationales for the proportional contribution of Y, C$_r$, and C$_b$ apply to establishing the C$_b$ matrix coefficients when generating the green and cyan image signals (here established as ~1 and ~4, respectively).

Figure 7:
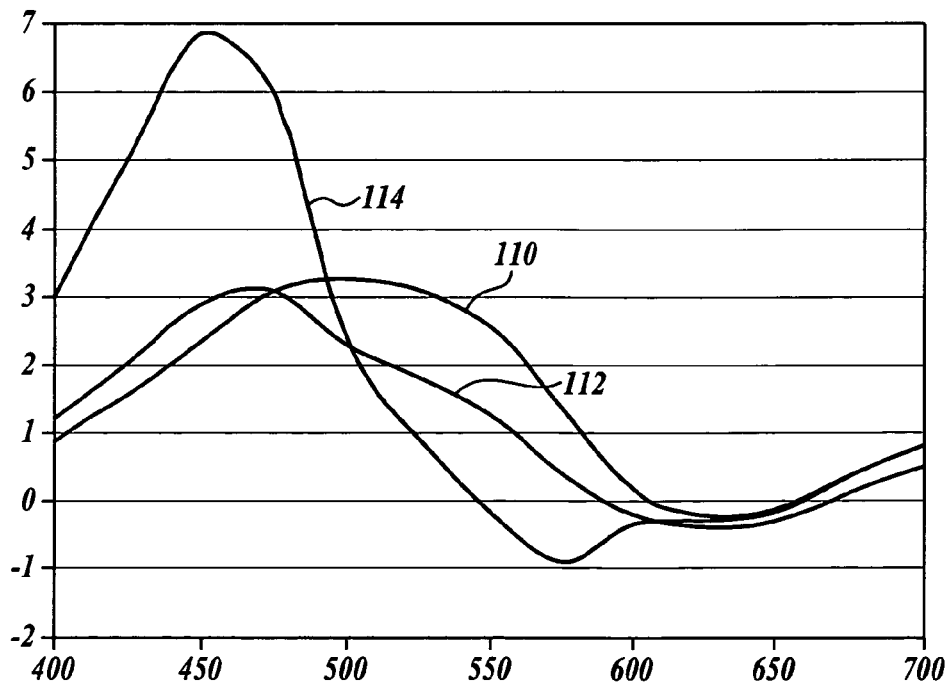
FIG. 7 shows a spectral plot of blue, cyan, and green image signals produced from a CMYG image sensor in accordance with one embodiment of the present invention.

FIG. 7 illustrates the spectral response of the green 110, cyan 112, and blue 114 signals calculated from the luminance and chroma difference signals using the color space transformation matrix described above. The calculated blue, cyan, and green response curves have peaks at approximately 450, 470, and 500 nanometers and a substantially reduced response for wavelengths greater than 600 nanometers. Once the blue, cyan, and green image signal values have been computed from the luminance and chroma difference signals, the image signal values can be stored in the color display memories and applied to the inputs of a color video monitor as described above.

The image processing techniques described herein can be implemented in software, such that switching between conventional full spectrum white light imaging mode and short wavelength imaging modes becomes a matter of selecting of the appropriate transformation matrix to eliminate the contribution of red light to the image signals, generating the image signal values to be assigned to the color display memories, and routing of the signals in the display memories to the appropriate input of the color video monitor. Such software implementation of a short wavelength imaging mode requires no moving mechanical, optical, or electrical parts.

Furthermore, since full spectrum white light images and short wavelength images generated by using image processing techniques, such as those described herein, are generated from the same broad band reflected white light signal transduced by the color image sensor, it is possible for an image processor with sufficient processing speed and image memory to generate images in both modes within the time of a single video frame. Image processors, such as the 6400 series of processors from Texas Instruments Corp., provide such processing speed and image memory. With such an image processor, within the time of a single video frame, a white light image (or RGB components of a white light image) can be computed from the image sensor signals and stored in one area of the display memory and a short wavelength image (or the color components of such an image) can be computed from a subset of image sensor signals (i.e. excluding the signal data from red light) and stored in another area of the display memory. The combined white light and short wavelength image data is then supplied to the inputs of a color video monitor so that both images are displayed simultaneously. Alternatively, the white light image signals and short wavelength image signals may be stored in separate display memories for simultaneous display on two separate color video monitors.

Figure 8:
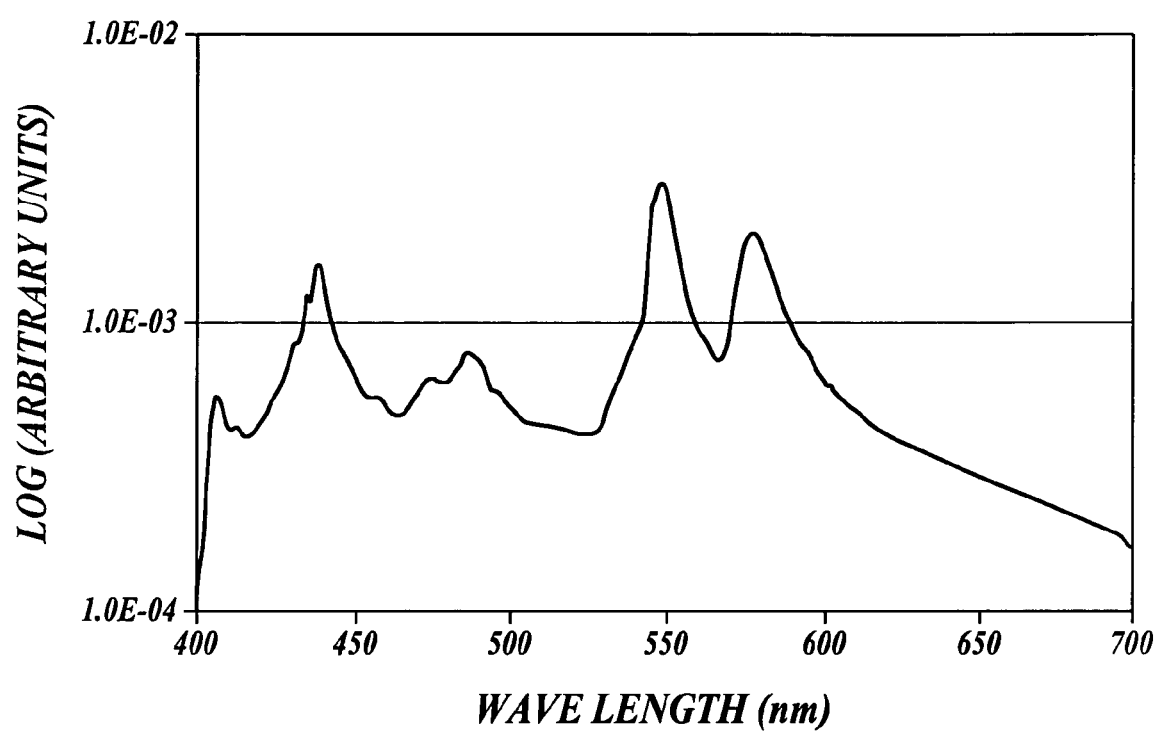
FIG. 8 is a spectral plot of a broadband illumination source for use with one embodiment of the present invention.

As indicated above, the present invention utilizes a broadband light source to perform both white light imaging and short wavelength imaging by substantially eliminating the component of the image due to red illumination light. In general, for the short wavelength imaging mode, it is also preferable that the light emitted by the endoscopic light source also have a significant blue and green light component. In one embodiment of the invention, a mercury arc lamp has been found to work well for use in providing the illumination light for both a full spectrum white light imaging mode and short wavelength imaging mode. FIG. 8 shows the spectral output of a typical mercury arc lamp having a substantial blue peak at approximately 437 nanometers and a substantial green peak at approximately 550 nanometers. However, other light sources could also be used to produce broadband illumination light for both the white light and short wavelength imaging modes, such as metal halide or other arc lamp technologies, or a series of spectrally spaced LEDs or laser diodes, etc.

While illustrative embodiments have been illustrated and described, it will be appreciated that various changes can be made therein without departing from the scope of the invention. For example, although the described embodiments of the invention use an endoscope to deliver and collect the image of the tissue, it will be appreciated that other medical devices such as fiber optic guidewires or catheters could also be used. Therefore, the scope of the invention is to be determined by the following claims and equivalents thereof.

The embodiments of the invention in which an exclusive property or privilege is claimed are defined as follows:

1. A system for producing images of tissue with a medical device that delivers an illumination light to a body cavity and a color image sensor that produces images of the tissue from a number of pixels that are sensitive to different wavelengths of light, comprising:

an image processor coupled to receive signals produced by the color image sensor in response to illumination light reflected from the tissue having red, green, and blue color components, wherein, the image processor calculates image signals that are stored in a memory by minimizing the contribution from signals produced by the image sensor in response to red illumination light.

2. The system of claim 1, wherein the image sensor is an RGB sensor having pixels that are primarily sensitive to red, green, and blue light, and wherein the image processor receives signals from each of the sensor pixels and computes the image signals for storage in the memory from the signals produced by the pixels that are sensitive to green and blue light only.

3. The system of claim 2, wherein the image processor computes signals to be stored in the memory by calculating a blue signal value from the signals produced by sensor pixels that are sensitive to blue light, a green signal value from the signals produced by sensor pixels that are sensitive to green light and the cyan signal value from a combination of the signals produced by sensor pixels that are sensitive to blue light and the signals produced by sensor pixels that are sensitive to green light.

4. The system of claim 3, wherein the image processor calculates the cyan signal value to be stored in the memory by averaging the signals produced by the pixels that are sensitive to blue light and green light.

5. The system of claim 3, wherein the calculated blue signal value, green signal value and cyan signal value stored in the memory are supplied to separate color inputs of a color video monitor.

6. The system of claim 5, where the calculated blue signal value, green signal value and cyan signal value stored in the memory are respectively supplied to blue, red, and green color inputs of the color video monitor.

7. The system of claim 1, wherein the image sensor is a CMYG sensor having pixels that are primarily sensitive to cyan, magenta, yellow, and green light, wherein the image processor computes luminance, red chroma difference and blue chroma difference values from CMYG pixel signals and converts the luminance, red chroma difference and blue chroma difference into blue, green, and cyan signal values and stores these signal values in the memory.

8. The system of claim 7, wherein the conversion of the luminance, red chroma difference, and blue chroma difference values to blue, green, and cyan signal values incorporates a subtraction of approximately 1.5 times the red chroma difference value from the luminance value.

9. The system of claim 8, wherein the conversion of the luminance, red chroma difference, and blue chroma difference values to blue, green, and cyan signal values incorporates a contribution from the blue chroma difference value to the green, cyan and blue signals in a ratio of approximately 1:4:6, respectively.

10. An imaging system for generating white light images and short wavelength visible images of tissue in response to a broad band illumination light that is delivered to a tissue sample and providing those images to one or more color video monitors, comprising:

an image sensor that receives reflected light from the tissue sample, the image sensor having a number of pixels sensitive to different wavelengths of light and which generate image signals in response to the light received from the tissue sample; and an image processor that receives a set of image signals from the image sensor and produces a white light image of the tissue sample from the set of image signals and a short wavelength image of the tissue sample from a subset of the image signals, wherein the short wavelength image of the tissue is produced by substantially eliminating a contribution of red light in the set of image signals.

11. The system of claim 10, wherein the image sensor is located at the distal end of an endoscope.

12. The system of claim 10, wherein the image sensor is located at the proximal end of an endoscope.

13. The system of claim 10, wherein the image sensor is an RGB sensor.

14. The system of claim 10, wherein the image sensor is a CMYG sensor.

15. The system of claim 10, wherein the image processor has sufficient processing speed and a display memory to process and provide for display both a white light image and a short wavelength image within a video frame.

16. The system of claim 15, wherein the white light image and the short wavelength image are simultaneously displayed on the same color video monitor.

17. The system of claim 15, wherein the white light image and the short wavelength image are simultaneously displayed on two separate color video monitors.

* * * * *